United States Patent [19]
Fong

[11] Patent Number: 5,871,021
[45] Date of Patent: Feb. 16, 1999

[54] DENTAL FLOSSING APPARATUS

[76] Inventor: Alex B. Fong, P.O. Box 488, San Leandro, Calif. 94577

[21] Appl. No.: 957,844

[22] Filed: Oct. 27, 1997

[51] Int. Cl.$^6$ .................................................... A61C 15/00
[52] U.S. Cl. .............................................................. 132/323
[58] Field of Search ..................................... 132/321, 323, 132/324, 310, 309

[56] References Cited

U.S. PATENT DOCUMENTS 5,305,768  4/1994  Gross et al. ............................ 132/321
5,680,875  10/1997  Winters .................................... 132/323
5,765,577  6/1998  Wei et al. ................................ 132/321

Primary Examiner—Cary E. O'Connor
Attorney, Agent, or Firm—Papan Devani, Esq; Thomas Powers, Ph.D.; Chandrakant C. Shroff

[57] ABSTRACT

A dental flossing apparatus, comprising a length of dental floss having two ends and two floss holders. One floss holder is attached to each end of the dental floss. Each floss holder comprises a flat piece of plastic having an edge with a continuous groove therein. The groove allows dental floss to be wrapped around the floss holder. Each floss holder is molded around one end of the dental floss, forming a very secure bond between the floss and the holder.

8 Claims, 6 Drawing Sheets

DENTAL FLOSSING APPARATUS

INTRODUCTION

The invention is a device to allow for the convenient flossing of one's teeth without requiring that bare floss be wrapped around one's fingers. More specifically, the invention consists of a dental flossing apparatus comprising a length of dental floss having handles securely attached to each end, and the method of making the same.

Dental floss having handles at each end is well-known in the prior art. However, many of these devices have the drawback that the handles can become detached from the floss, forcing the user to either replace the dental floss or wrap the ends of the floss having no handles around his fingers, possibly impairing blood flow to his fingertips.

It is an object of this invention to attach handles to dental floss in such a way that the handles cannot readily become detached.

SUMMARY OF THE INVENTION

The invention is a dental flossing apparatus comprising a length of dental floss having two ends; and two floss holders, one attached to each end of the length of dental floss. Each floss holder comprises a flat piece of plastic having an edge with a continues groove therein, at least part of which is a piece of plastic which has been molded around an end of the length of dental floss. The groove is adapted to allow dental floss to be fitted into the groove and wrapped around the floss holder. This allows the user to adjust the length of the dental floss he is using to clean his teeth without having to wrap it around his fingers. By molding the handle around the dental floss, a very secure bond is formed between the handle and the floss.

DESCRIPTION OF THE DRAWINGS

In FIG. 9b, a portion of the floss holder is cut away for clarity.

DETAILED DESCRIPTION OF THE INVENTION

Figure 1:
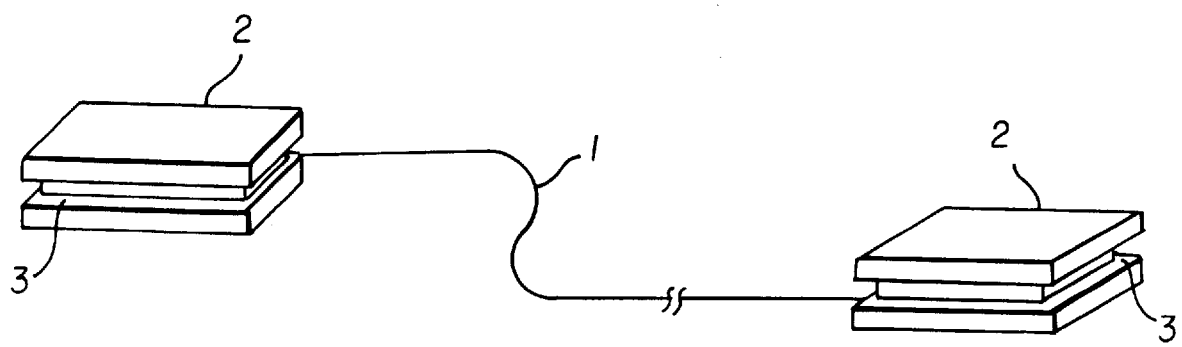
FIG. 1 shows a first embodiment of the inventive dental flosser having two floss holders.

The invention is a dental flosser (shown in FIG. 1), comprising a length of dental floss 1 having two ends; and two floss holders 2, one attached to each end of the length of dental floss. Each floss holder comprises a flat piece of plastic having an edge with continuous groove therein 3. Each floss holder is formed from one or more pieces of plastic, at least one of which has been molded around an end of the length of dental floss. To adjust the length of the length of dental floss, dental floss may be fitted into the groove and wrapped around the floss holder. Each floss holder may additionally comprise a means for preventing floss which has been wrapped around the floss holder from unwrapping.

Figure 2:
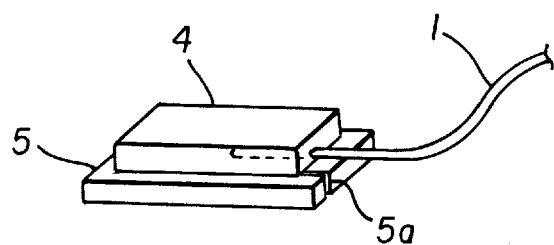
FIGS. 2 and 3 show the pieces used to make each dental floss holder in the dental flosser of FIG. 1.

The dental flosser is made by taking a defined length of dental floss 1 and placing each end of the dental floss into an injection mold. Molten plastic is then injected into the mold and a first floss holder side is molded around the dental floss. The first floss holder side is then removed from the mold, with the dental floss securely attached thereto. First floss holder sides can be molded onto both ends simultaneously, using separate molds, or sequentially, using the same mold for each. The first floss holder side 4, shown in FIG. 2, is a flat piece of plastic having two faces, one of which has a recessed edge 5. The piece of dental floss 1 emerges from the edge of the first floss holder side (In FIG. 2, the portion of floss 1 which is buried within piece 4 is shown in dotted lines.). The precise shape of the first floss holder side is unimportant; it can be shaped like a rectangle (as shown in FIG. 2), a square, or any other polygon. It can also be circular, oval, or heart-shaped. It is preferred that the floss emerges from the recessed edge of the first floss holder side.

Figure 3:
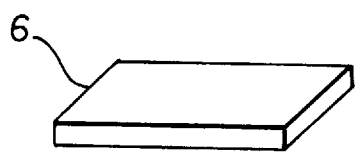

Next, two second floss holder sides are prepared from molten plastic in a second injection mold. Each of the second floss holder sides 6, shown in FIG. 3, is the same size and shape as the first floss holder sides, and comprises a flat piece of plastic having two faces. However, these are not molded around dental floss. One face of each of the second floss holder sides is then bonded to the side of a first floss holder side having a recessed edge. Preferably, this is done by heat-sealing the two together.

Figure 4A:
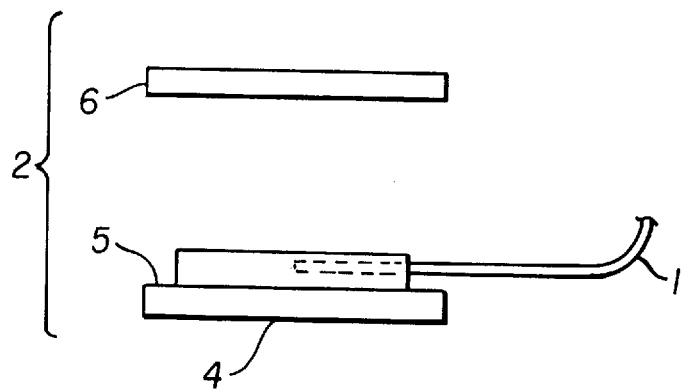
FIG. 4a is an exploded view of the floss holder showing how the pieces of FIGS. 2 and 3 fit together to make a dental floss holder.
Figure 4B:
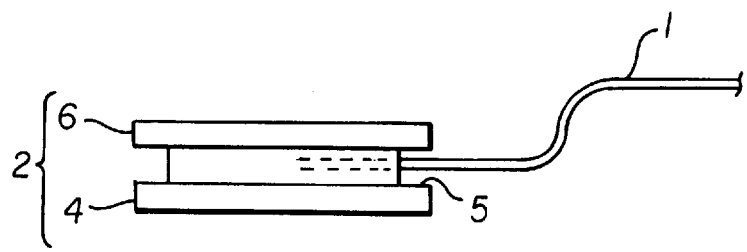
FIG. 4b is a view of the completed floss holder.

This melts the two floss holder sides together to form a single piece of plastic having a continuous groove around the edge. This groove, which is large enough to receive dental floss, is defined by the bonded face of the second floss holder side 6 on one side, and by the recessed edge 5 of the first floss holder side 4 on the other (as shown in FIGS. 4a and 4b). Preferably, the dental floss emerges from the interior of the groove in the floss holder.

Figure 5:
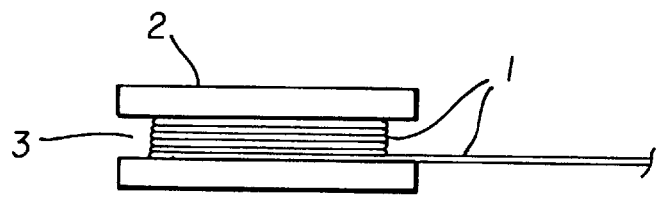
FIG. 5 shows how to adjust the length of the dental floss by wrapping the floss around the dental floss holder.

The length of dental floss used to manufacture the invention is preferably from 6 to 7 inches long, although the floss may be longer or shorter if desired. The length of floss may be adjusted by the user by wrapping part of the floss around the floss holder 2 several times, as shown in FIG. 5. The wrapped portion of the floss should be fitted into the groove 3 between the first and second floss holder sides.

One problem with simply wrapping the floss around the floss holder to adjust the dental floss length is that it may unwrap in between uses. This necessitates a readjustment of the length of unwrapped dental floss to the user's preferred length each time the device is used. As dental floss is normally only used by one person at a time for sanitary reasons, it would be greatly appreciated by the user if the wrapped portion of the dental floss could be secured to keep it from unwrapping.

This can be done by simply cutting a small slit 5a in the recessed edge 5 of the first floss holder side 4 (FIG. 2). The width of the slit should be less than the thickness of the dental floss. After the first floss holder side is heat-sealed to the second floss holder side, a floss holder 2 having a slit 5a is obtained. After the floss has been wrapped around the floss holder until the length of free floss has been adjusted to a desired length, the floss may be pulled into the slit. The sides of the slit will grip the floss, holding it and preventing the wrapped floss from unwrapping. However, it is easy to accidentally pull the floss out of the slit and loosen the wrapped floss.

Figure 6A:
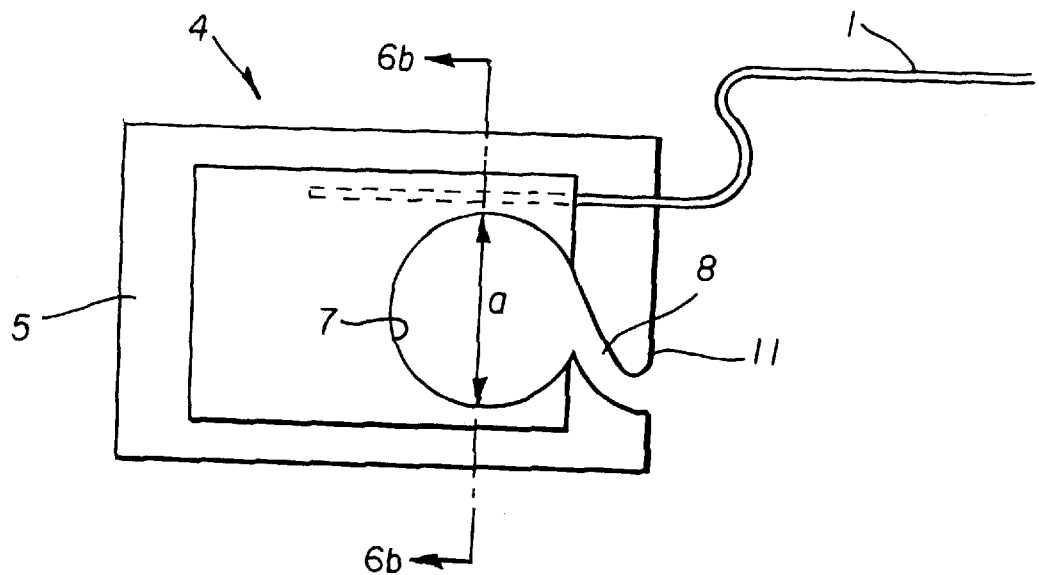
FIGS. 6a, 6b, 7a and 7b illustrate the parts required to make a second embodiment of the inventive dental floss holder.
Figure 6B:
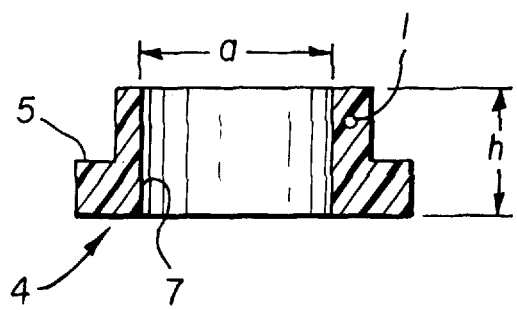
Figure 7A:
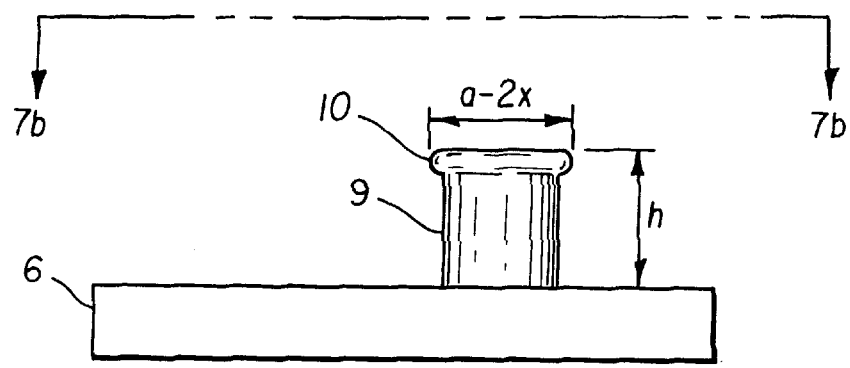
Figure 7B:
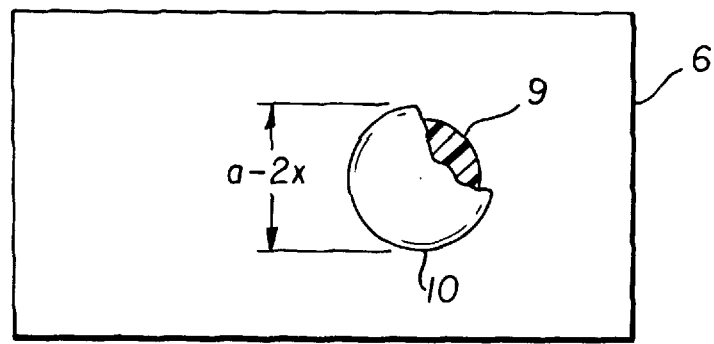

In a preferred embodiment which avoids the problem of accidentally loosening wrapped floss, the first floss holder side 4 may be molded with a hole 7 therethrough, said hole having a first diameter a, as shown in FIGS. 6a and 6b. A slit 8 runs from the hole to the edge of the first floss holder side. The slit is wide enough to allow a piece of dental floss to pass through the slit into the hole. The second floss holder side 6 may be molded with a post 9 having a diameter of a−2x and a height h, where x is the thickness of the dental floss and h is the thickness of the first floss holder side, on one face thereof (FIGS. 7a and 7b). Preferably, the post 9 is shaped like a mushroom, with the top 10 of the pole being wider than the bottom of the pole.

Figure 8A:
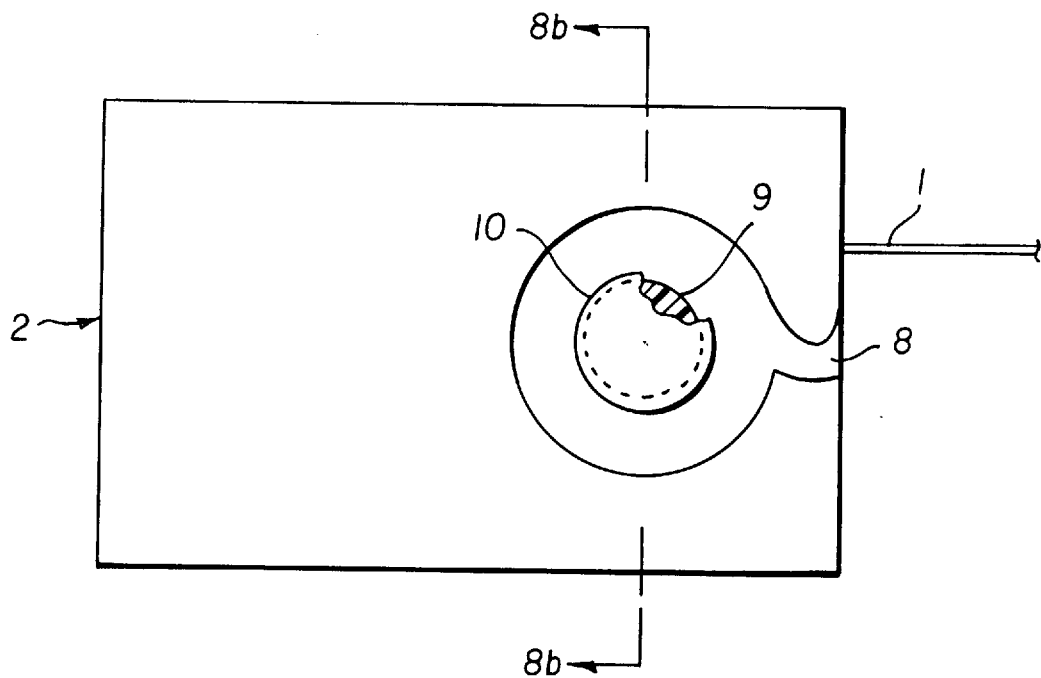
FIGS. 8a and 8b illustrate a second embodiment of the dental floss holder, made using the parts shown in FIGS. 6a through 7b.
Figure 8B:
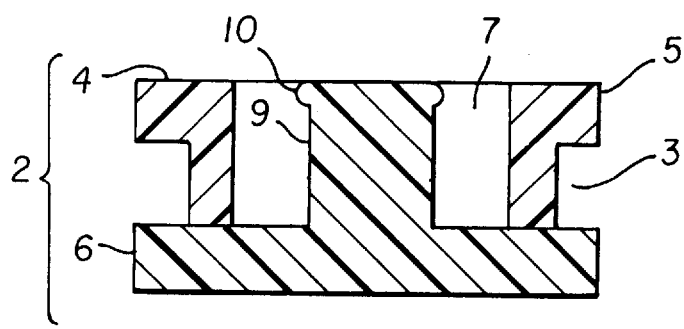

When the first and second floss holder sides are bonded together to make a floss holder 2, they are positioned so that the post 9 goes through the hole 7, as shown in FIGS. 8a and 8b. There is a space at least equal to the thickness of the dental floss between the inside edge of hole 7 and post 9. The resulting floss holder 2 comprises a flat piece of plastic having an edge with a continuous groove adapted to receive dental floss therein. The hole 7 in the first floss holder side and the face of the second floss holder side 6 having the pole 9 thereon define a round pit of diameter a and depth h in the floss holder. The round post 9 of diameter a−2x and height h is centered on the bottom of the round pit. The slit 8 now leads from the edge of the floss holder to the round pit. Preferably, the slit in the floss holder meets the round pit tangentially. This forms a tongue or tab 11 which overhangs the groove in the floss holder.

Figure 9A:
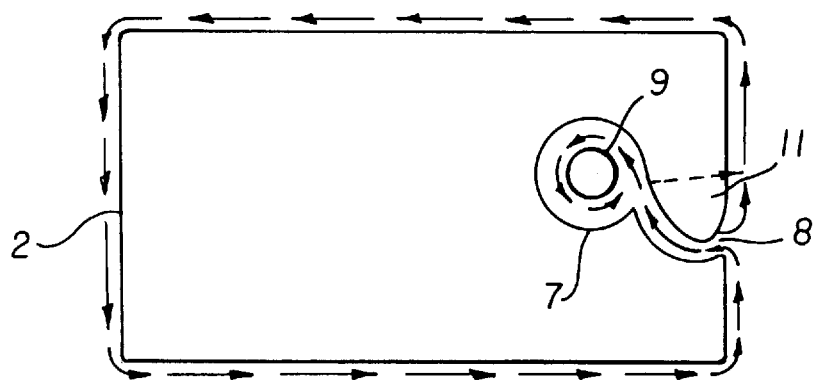
FIGS. 9a and 9b show how floss is held on the second embodiment of the dental floss holder.
Figure 9B:
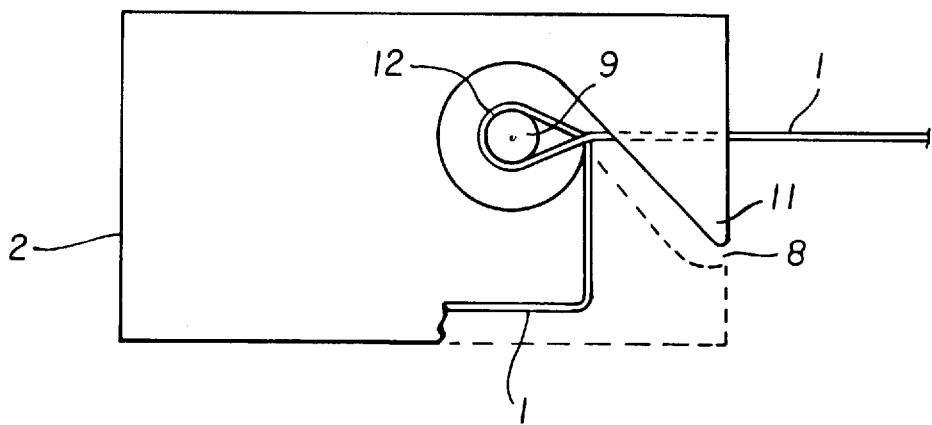

Then, the dental floss which is left free after wrapping the dental floss around the groove in the floss holder may be pulled through the slit in the floss holder into the round pit and wrapped around the post going through this pit. This is illustrated in FIG. 9a, with the direction of motion of the floss being shown by the dashed arrow. At least one complete turn 12 of floss should be wrapped around the post. The widened top end of the post prevents the turn 12 of floss from sliding off the post. The floss is then passed back through the slit and pulled tight. This effectively prevents the floss wrapped around the floss holder from unwrapping. After the floss is passed back through the slit, it may be positioned under the tongue 11 before being pulled tight (FIG. 9b; note that a portion of the floss holder overlying the peripheral groove is cut away for clarity). Positioning the dental floss under the tongue in this manner prevents the dental floss from being pulled through the slit accidentally.

The dental floss may be freed from post 9 by pulling the floss back through the slit 8 into the round pit. The floss is then unwrapped from the post. The floss may then be unwrapped from the groove.

As an additional feature, designed to prevent the two floss folder sides from moving when they are heat-sealed together, two small holes may be provided on the first floss holder side and two pins adapted to fill these holes may be provided on the second floss holder side. When the pins are fitted into the small holes, relative movement between the floss holder sides is prevented.

What is claimed is:

1. A device for flossing teeth, comprising:
   a) a length of dental floss having two ends; and
   b) two floss holders, one attached to each end of the length of dental floss;
      wherein each floss holder comprises a flat piece of plastic having an edge with a continuous groove adapted to receive dental floss therein; a round pit of diameter a and depth d in the floss holder, said pit having a defined bottom; a round post of diameter a−2x and height h, where x is the diameter of the dental floss and h is at least equal to d, said post being mounted on the bottom of said pit; and a slit of width x leading from the edge of the floss holder to the round pit;
      wherein said slit is adapted to permit said length of dental floss to pass therethrough and into said round pit; and said round post is adapted to allow the length of dental floss within the round pit to be wrapped around said round post;
      and wherein each floss holder additionally comprises a means for preventing dental floss which has been wrapped around the round post from sliding off of the post.

2. The device of claim 1, wherein said means for preventing dental floss which has been wrapped around the round post from sliding off of the post comprises a flared upper end of said post.

3. The device of claim 2, wherein said slit intersects the round pit tangentially.

4. The device of claim 1, wherein said slit intersects the round pit tangentially.

5. The device of claim 1, wherein each floss holder is formed by the steps of:
   a) obtaining a plastic first floss holder side having a post of diameter a−2x and height h mounted thereon;
   b) obtaining a plastic second floss holder side of thickness h which has been molded around the end of the length of dental floss; wherein said second floss holder side has a hole of diameter a passing therethrough, a recessed edge, and a slit passing from the recessed edge to the hole of diameter a; and
   c) heat-sealing the first floss holder side to said second floss holder side so that (i) the groove in the floss holder is defined by a space between the recessed edge of the second floss holder side and the first floss holder side; and (ii) the post on the first floss holder side passes through the hole in the second floss holder side.

6. The device of claim 1, wherein each floss holder comprises a flat piece of plastic having a defined shape.

7. The device of claim 6, wherein the defined shape is polygonal, circular, oval, or heart-shaped.

8. A method of forming a device for flossing teeth, comprising the steps of:
   a) obtaining a length of dental floss having a first end and a second end;
   b) obtaining a plastic first floss holder side having a post of diameter a−2x and height h mounted thereon;
   c) molding a plastic second floss holder side of thickness h around the first end of the length of dental floss; wherein said second floss holder side has a hole of diameter a passing therethrough, a recessed edge, and a slit passing from the recessed edge to the hole of diameter a;
   d) heat-sealing the first floss holder side to said second floss holder side so that (i) a groove in the floss holder is defined by a space between the recessed edge of the second floss holder side and the first floss holder side; and (ii) the post on the first floss holder side passes through the hole in the second floss holder side; and
   e) repeating steps (b), (c), and (d), providing that, when step (c) is repeated, the second floss holder side is molded around the second end of the length of dental floss.

* * * * *